US00PP09920P

United States Patent [19]

Schumann et al.

[11] Patent Number: Plant 9,920

[45] Date of Patent: Jun. 10, 1997

[54] GERANIUM PLANT NAMED FISPINK

[75] Inventors: Ingeborg Schumann, Albstadt; Angelika Utecht, Montabaur, both of Germany

[73] Assignee: Florfis AG, Binningen, Switzerland

[21] Appl. No.: 532,505

[22] Filed: Sep. 22, 1995

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Foley & Lardner

[57] ABSTRACT

A new and distinct cultivar of geranium plant named Fispink, characterized by its bright pink flower color, single flower form, uniform green foliage without zonation, vigorous growth, good branching ability, relatively early flower response and rich flowering throughout the year.

2 Drawing Sheets

The present invention comprises a new and distinct cultivar of geranium, botanically known as *Pelargonium peltatum l'Hert,* and hereinafter referred to by the cultivar name Fispink.

Fispink is a product of a planned breeding program which had the objective of creating new ivy geranium cultivars with single flowers, vigorous growth, good branching ability, and in various flower colors.

Fispink was originated from a hybridization made by inventor Ingeborg Schumann in a controlled breeding program in Galdar, Gran Canaria, Spain in 1986. The female parent was an unnamed hybrid seedling obtained by crossing the cultivars Italian Gem and El Gaucho. Italian Gem has violet pink semi-double to double flowers with comparatively dark green, zoned foliage, while El Gaucho is characterized by salmon pink semi-double flowers and medium green leaves without zonation. The male parent of Fispink was a red single flowering plant of unknown origin.

Fispink was discovered and selected as one flowering plant within the progeny of the stated cross by inventor Angelika Utecht in 1991 in a controlled environment in Galdar, Gran Canaria, Spain.

The first act of asexual reproduction of Fispink was accomplished when vegetative cuttings were taken from the initial selection in June 1991 in a controlled environment in Galdar, Gran Canaria, Spain, by, or under the supervision of, inventor Angelika Utecht.

Horticultural examination of plants grown from these cuttings initiated in May 1992 in Hillscheid, Federal Republic of Germany, and containing thereafter, has demonstrated that the combination of characteristics as herein disclosed for Fispink are firmly fixed and are retained through successive generations of asexual reproduction.

Fispink has not been observed under all possible environmental conditions. The phenotype may vary significantly with variations in environment such as temperature, light intensity and daylength, without, however, any variance in genotype. The following observations, measurements, and comparisons describe plants grown in Hillscheid, Federal Republic of Germany under greenhouse conditions which approximate those generally used in commercial practice.

The following traits have been repeatedly observed and are determined to be basic characteristics of Fispink, which, in combination, distinguish this geranium as a new and distinct cultivar:

1. Bright pink flower color, with the upper petals having purple markings.
2. Single, medium sized flowers.
3. Medium green foliage without zonation.
4. Medium to vigorous growth and well branched plant habit.

5. Early to medium flower response, and rich flowering throughout the year.

Of the many commercial cultivars known to the present inventors, there is none to which Fispink can be closely compared. The combination of flower color and lack of zonation is novel in cultivars of this species.

The accompanying photographic drawings show typical flower and foliage characteristics of Fispink, with colors being as true as possible with illustrations of this type.

The photo on Sheet 1 is of a plant of Fispink in a hanging basket.

The photo on Sheet 2 is an enlarged showing of the foliage and flowers.

In the following description, color references are made to The Royal Horticultural Society (R.H.S.) Colour Chart. The color values were determined indoors in May from plants grown indoors in Hillscheid, Federal Republic of Germany.

Classification:

*Botanical.*—A hybrid of the species *Pelargonium peltatum l'Hert.*

*Commercial.*—Ivy geranium, cv., Fispink.

INFLORESCENCE

Umbel:

*Shape.*—Irregular.

*Average diameter.*—115 mm.

*Average depth.*—65 mm.

*Peduncle length.*—155 mm.

*Color of peduncle.*—Light green, 137 D.

*Pedicel length.*—38 mm.

*Pedicel color.*—Light to dark red.

*Number of flowers per umbel.*—9.5.

*Number of flowers per umbel.*—The plant produces a very high number of umbels, continuing throughout the blooming season.

Corolla:

*Average diameter.*—43 mm.

*Form.*—Single, nearly round.

*Number of petals.*—5.

*Number of petaloids.*—None.

*Color (general tonality from a distance of three meters)* .—Bright pink.

*Color of upper surface of petals.*—57 C, with occasional salmon tint between 57 C and 58 C–D.

*Color of lower surface of petals.*—58 D or lighter.

*Markings of two upper petals.*—Veins of purple, connected at the tops with a small red spot; veins and spot surrounding an elongated white fleck. Markings are essentially confined to the claw portion of the top surface.

*Markings of three lower petals.*—Lower petal top surfaces have a weak or very weak red spot on each petal.

*Color of sepals.*—Light green, largest sepal red (anthocyanin).

*Number of sepals.*—5.

Bud:

*Shape.*—Narrow elliptical.

*Color (adaxial).*—Medium green.

*Color (abaxial).*—Light salmon to pink.

Reproductive organs:

*Androecium.*—7 fertile anthers; white filaments, yellow-orange pollen.

*Gynoecium.*—5-lobed stigma, pink, with white filament.

*Seed.*—Seed set may occur outdoors.

Spring flowering response period: In Hillscheid, Germany, in 1993 plants had on average 1.5 umbels with at least one flower opened 15 weeks after planting of unrooted cuttings (pinched plants).

Outdoor flower production: The flower count in 1994 in Hillscheid, Germany, indicated about 125 umbels per plant for May through August observation period.

Durability: Shatter resistance average for single flowered varieties; good rain and heat tolerance.

PLANT

Foliage:

*Form.*—Ivy shaped with slightly rounded lobes.

*Margin.*—Mainly entire, slightly crenated near the tips of lobes.

*Surface of leaf.*—Flat, smooth, slightly glossy.

*Size of leaf.*—85 mm.

*Color of upper surface.*—Medium green, approximately 137 C.

*Color of zonation.*—No zonation.

*Tolerance of botrytis.*—Good.

General appearance and form:

*Internode length.*—4–5 cm.

*Branching pattern.*—4.1 branches per week.

*Length of plants.*—85 cm (in September, 35-week-old plants).

Ploidy: Tetraploid.

It is claimed:

1. A new and distinct cultivar of geranium plant named Fispink, as illustrated and described.

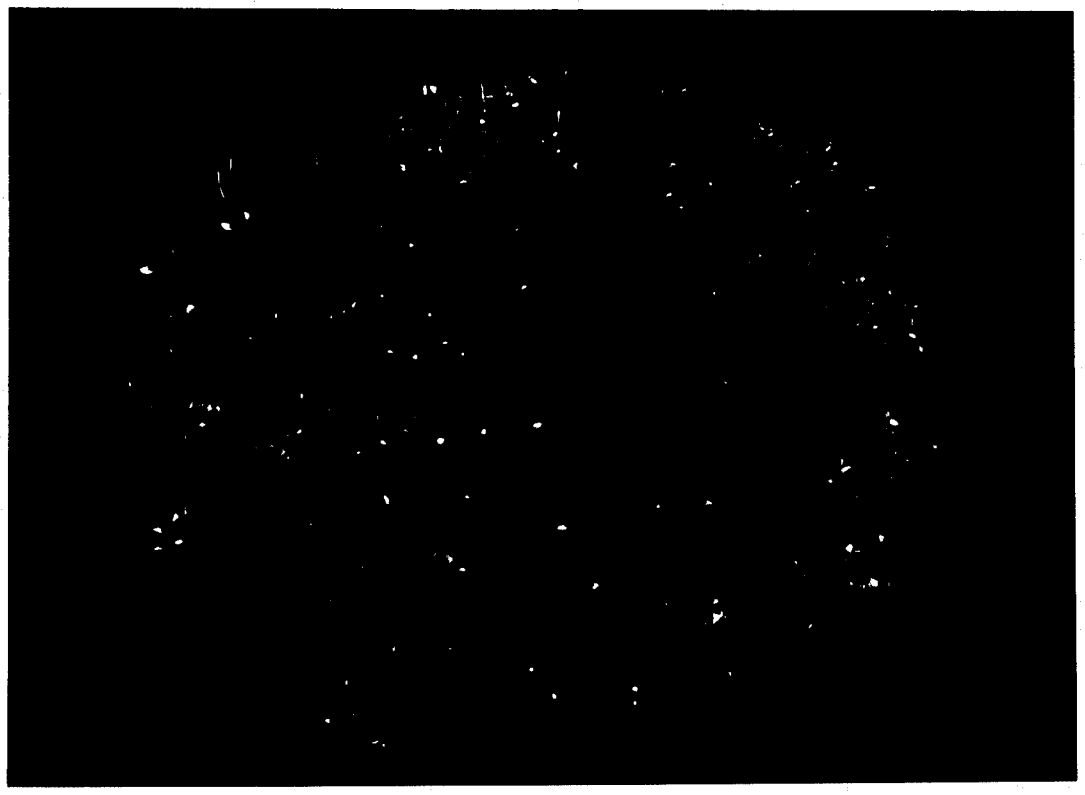

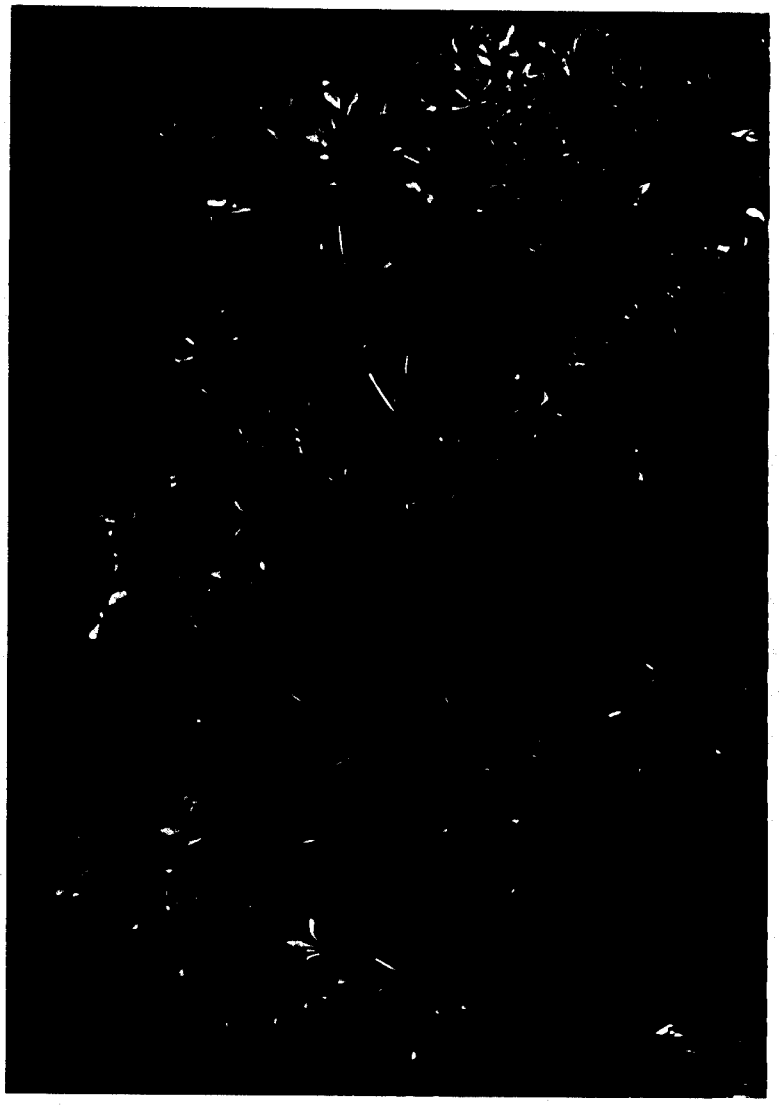

* * * * *